(12) United States Patent
Miike et al.

(10) Patent No.: US 11,896,302 B2
(45) Date of Patent: Feb. 13, 2024

(54) CAUTERY DEVICE AND CAUTERY SYSTEM

(71) Applicant: NeuroLightech Inc., Tokyo (JP)

(72) Inventors: Shinya Miike, Tokyo (JP); Kazuo Shimizu, Tokyo (JP)

(73) Assignee: NeuroLightech Inc., Tokyo (JP)

( * ) Notice: Subject to any disclaimer, the term of this patent is extended or adjusted under 35 U.S.C. 154(b) by 0 days.

(21) Appl. No.: 17/730,620

(22) Filed: Apr. 27, 2022

(65) Prior Publication Data

US 2022/0346877 A1 Nov. 3, 2022

(30) Foreign Application Priority Data

Apr. 28, 2021 (JP) .................................. 2021-076649

(51) Int. Cl.
*A61B 18/22* (2006.01)
*A61B 18/20* (2006.01)
*A61B 18/00* (2006.01)

(52) U.S. Cl.
CPC ............. *A61B 18/22* (2013.01); *A61B 18/203* (2013.01); *A61B 2018/00452* (2013.01); *A61B 2018/00636* (2013.01)

(58) Field of Classification Search
CPC ............................... A61B 18/22; A61B 18/203

USPC ........................................................ 607/89
See application file for complete search history.

(56) References Cited

U.S. PATENT DOCUMENTS 6,530,919 B1 * 3/2003 Chodorow ........... A61B 18/203
606/13

FOREIGN PATENT DOCUMENTS

JP 6301926 B2 3/2018

* cited by examiner

*Primary Examiner* — Nadia A Mahmood
(74) *Attorney, Agent, or Firm* — Harness, Dickey & Pierce, P.L.C.

(57) ABSTRACT

A cautery device for biological tissue, includes: a probe including a head unit that is configured to be inserted into a living body to emit light to cauterize the biological tissue, the head unit including a first fixing member, a second fixing member, and an exit hole, the exit hole being located between the first fixing member and the second fixing member, the exit hole allowing the light to be emitted therethrough; and an elongated catheter configured to sandwich the biological tissue between the probe and the catheter, to thereby support the biological tissue, the catheter including a third fixing member configured to fix the first fixing member and a fourth fixing member configured to fix the second fixing member.

6 Claims, 11 Drawing Sheets

CAUTERY DEVICE AND CAUTERY SYSTEM

CROSS-REFERENCE TO RELATED APPLICATION

The present application claims priority pursuant to 35 U.S.C. § 119 from Japanese patent application number 2021-076649 filed on Apr. 28, 2021, the entire disclosure of which is hereby incorporated by reference herein.

BACKGROUND

Technical Field

The present disclosure relates to cautery devices and cautery systems.

Description of Related Art

Devices for cauterizing biological tissue with light radiation are known. For example, a device described in U.S. Pat. No. 6,530,919 is capable of inducing thermal coagulation of biological tissue using light directed from a light source to one end of a rod-shaped light guide and emitted through the other end of the light guide. Alternatively, a catheter system described in Japanese Patent No. 6301926 includes an ablation catheter having a plurality of electrodes that apply ablation energy to biological tissue to thereby ablate it.

However, when uniform cauterization of a given area of biological tissue is desired, it is difficult for the devices described in U.S. Pat. No. 6,530,919 and the systems described in Japanese Patent No. 6301926 to achieve this. For example, when the thickness of a given area of biological tissue to be cauterized varies in part, a portion that is thicker than other portion thereof may not be able to be cauterized because light is less likely to reach the inside of the thicker portion. In addition, insufficient cauterization may be caused by insufficient cauterizing temperature resulting from the blood flowing in blood vessels.

SUMMARY

An aspect of an embodiment of the present disclosure is a

Other features of the present disclosure will become apparent from the description in the present specification and the accompanying drawings.

DETAILED DESCRIPTION

First Embodiment

==Cautery Systems==

Figure 1:
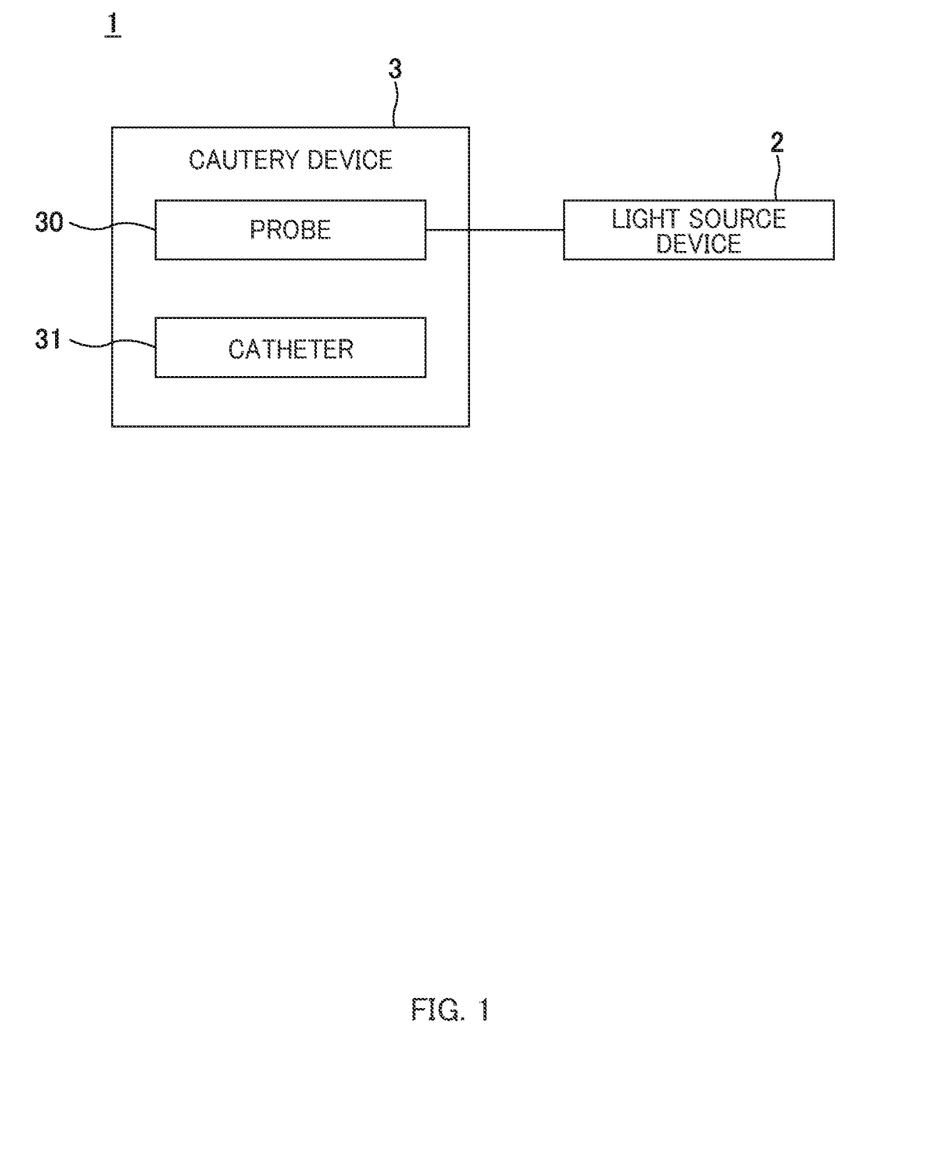
FIG. 1 is a block diagram for explaining a configuration of a cautery system according to a first embodiment.

FIG. 1 is a block diagram for explaining a configuration of a cautery system 1 according to an embodiment of the present disclosure. The cautery system 1 includes a light source device 2 and a cautery device 3.

[Light Source Device]

The light source device 2 produces light for cauterizing biological tissue. The light source device 2 has a light source that produces light in a wavelength range suitable for light absorption/scattering properties of tissue to be cauterized. Specifically, the light source used includes, for example, a laser light source, an LED light source, a halogen lamp, and a xenon lamp.

[Cautery Device]

Figure 2:
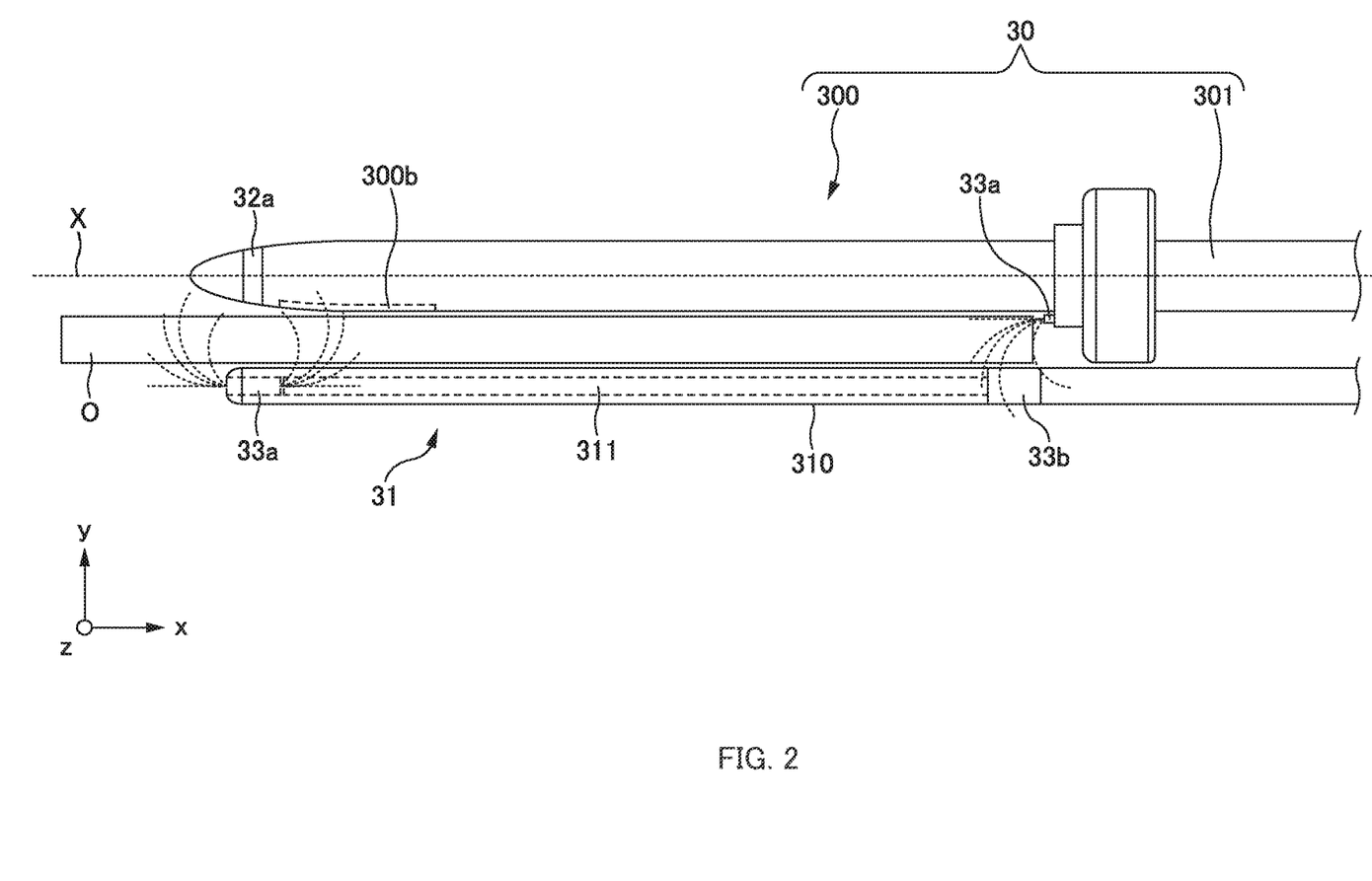
FIG. 2 is a diagram for explaining a structure of a cautery device according to a first embodiment.
Figure 3:
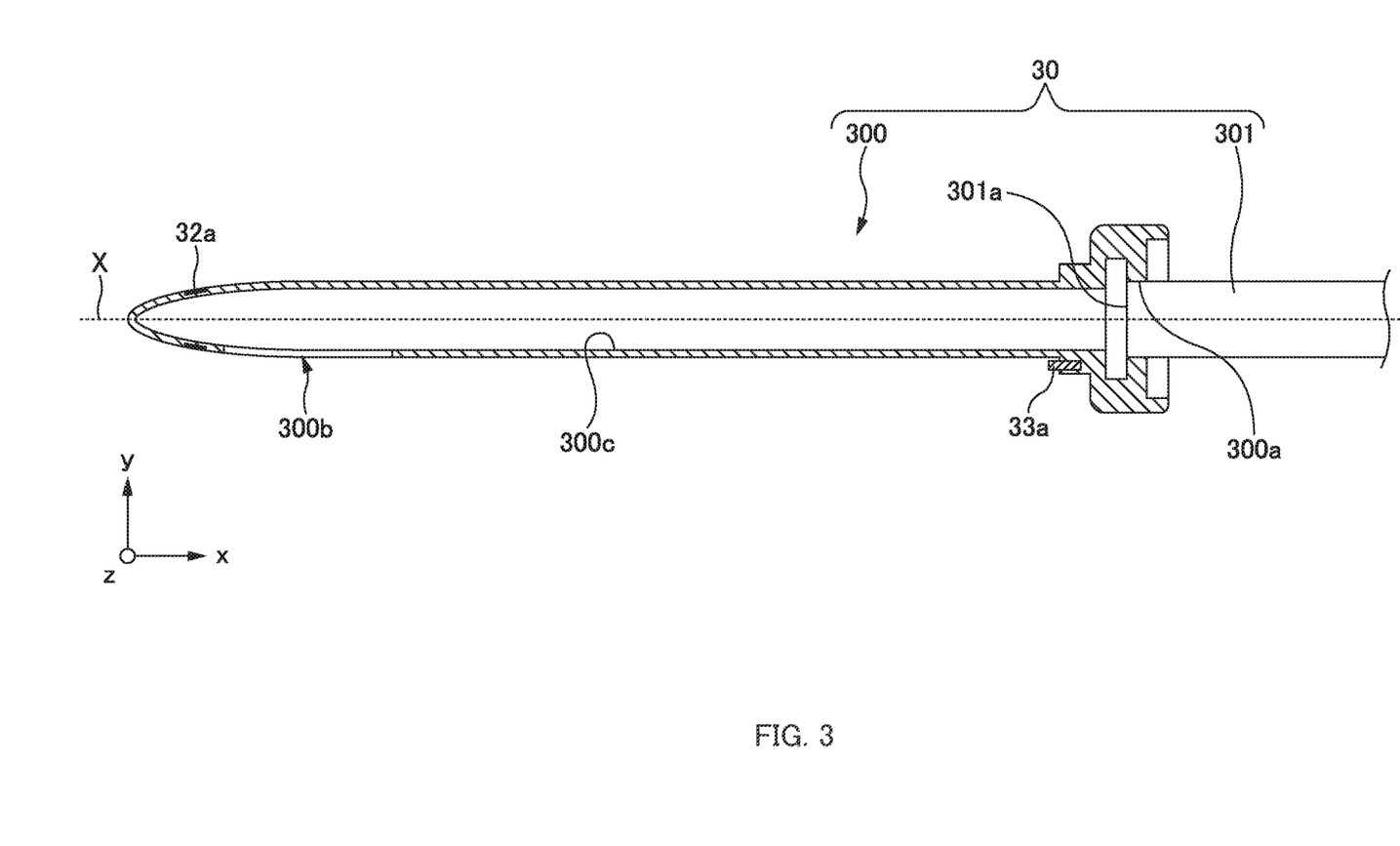
FIG. 3 is a cross-sectional view for explaining a structure of a probe according to a first embodiment.
Figure 4:
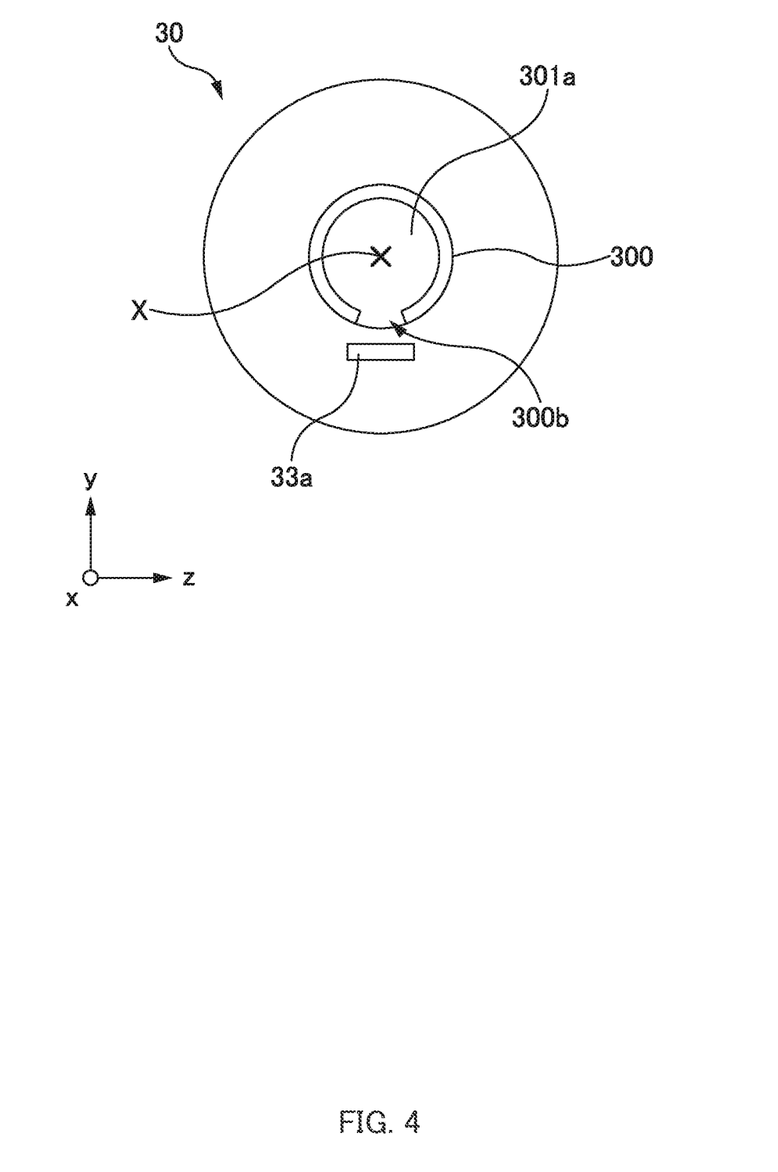
FIG. 4 is a cross-sectional view for explaining a structure of a probe according to a first embodiment.
Figure 5:
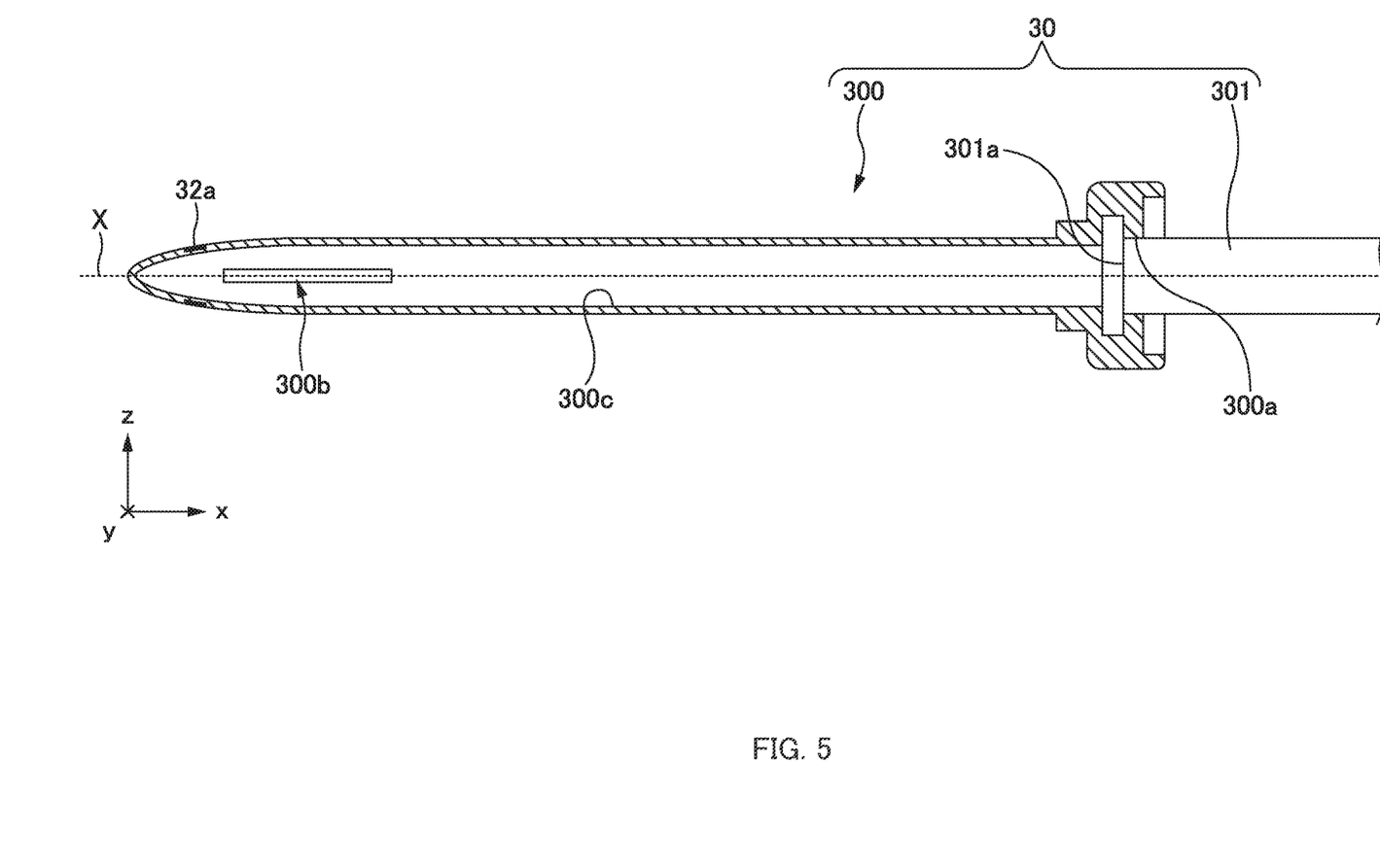
FIG. 5 is a cross-sectional view for explaining a structure of a probe according to a first embodiment.
Figure 6:
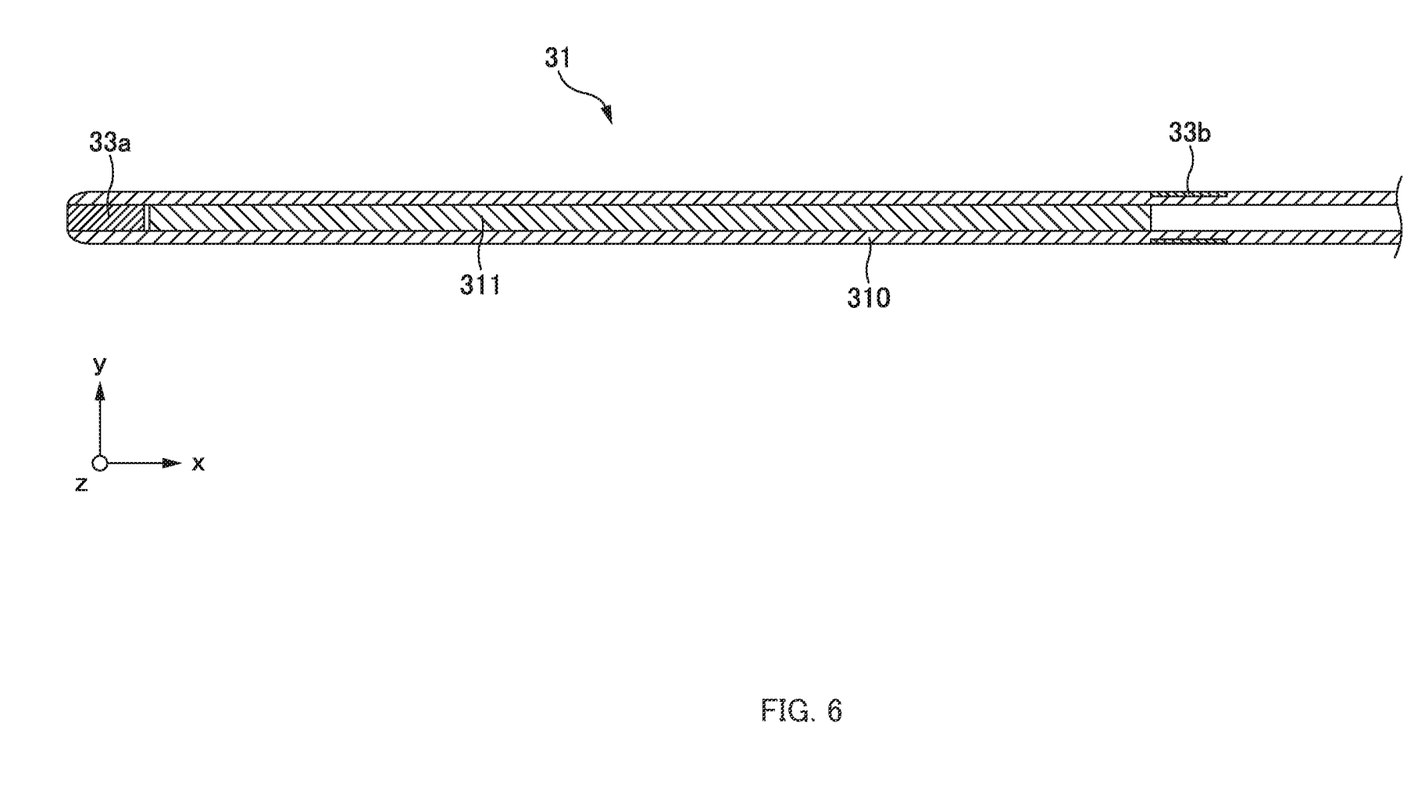
FIG. 6 is a cross-sectional view for explaining a structure of a catheter according to a first embodiment.

The cautery device 3 collects light from the light source device 2 and emits the light to biological tissue. Biological tissue is cauterized with the emitted light. The cautery device 3 includes a probe 30 and a catheter 31. Referring to FIGS. 2 to 6, the probe 30 and the catheter 31 will be described. FIG. 2 is a diagram for explaining a structure of the cautery device 3 according to an embodiment of the present disclosure. FIGS. 3 to 5 are cross-sectional views for explaining a structure of the probe 30 according to an embodiment of the present disclosure. FIG. 6 is a cross-sectional view for explaining a structure of the catheter 31 according to an embodiment of the present disclosure. The following description uses an orthogonal coordinate system in which x-, y-, and z-axes meet at right angles to one another, illustrated in FIGS. 2 to 6.

<Probe>

The probe 30 has a head unit 300 and a light guide unit 301 (FIGS. 2, 3, and 5).

The light guide unit 301 is an elongated member, such as an optical fiber, allowing the light from the light source device 2 to travel therethrough. The light guide unit 301 has one end coupled to the light source device 2 (not shown), and the other end coupled to the head unit 300 (FIGS. 2 to 5). The light that has entered the light guide unit 301 through its one end from the light source device 2 travels through the light guide unit 301 and enters the head unit 300.

In the following description, one end of the light guide unit 301 is referred to as a "distal end portion of the light guide unit 301." The face of the distal end portion of the light guide unit 301 from which the light from the light source device 2 is emitted is referred to as an "end face 301a." In an embodiment of the present disclosure, the end face 301a of the light guide unit 301 is flat.

The head unit 300 is a member that is to be inserted into a living body and emits light for cauterizing a given area of biological tissue O (see FIG. 2). The head unit 300 in an embodiment of the present disclosure has a central axis X and has substantially rotational symmetry around the central axis X. In FIGS. 2 to 5, the head unit 300 is illustrated with the central axis X parallel to the x-axis.

The head unit 300 has a hollow cylindrical shape with its length parallel to the central axis X and its two end portions spaced apart from each other in the direction of the central axis X. One end portion of the head unit 300 is closed.

The head unit 300 has one end portion having a convex, semi-ellipsoid shape, and the other end portion having formed therein an entrance hole 300a, which will be described later. The main body of the head unit 300 is of a hollow cylindrical shape having a rotational symmetry around the central axis X.

In the following description, the closed end portion of the head unit 300 is referred to as a "distal end portion of the head unit 300." The end portion having formed therein the entrance hole 300a, which will be described below, is referred to as a "proximal end portion of the head unit 300."

The head unit 300 has the entrance hole 300a, an exit hole 300b, a first reflector 300c, a first fixed member 32a, and a second fixed member 32b.

The entrance hole 300a is an opening formed in the head unit 300. By inserting the end portion of the light guide unit 301 into the entrance hole 300a, the head unit 300 is coupled to the light guide unit 301. This allows the light that has been emitted through the end face 301a of the light guide unit 301 to enter the head unit 300.

The entrance hole 300a in an embodiment of the present disclosure has a circular shape with a predetermined radius. The entrance hole 300a is arranged such that the central axis X passes through the center of the entrance hole 300a. The predetermined radius in an embodiment of the present disclosure is equal to the radius of the light guide unit 301.

The exit hole 300b is an opening formed in the side surface of the head unit 300. The exit hole 300b in an embodiment of the present disclosure is formed in the side surface of the main body of the head unit 300. The exit hole 300b allows the light that has entered the head unit 300 to be emitted to the outside. The light that has entered the head unit 300 is the light directed from the light source device 2 through the end face 301a of the light guide unit 301. The exit hole 300b in an embodiment of the present disclosure has a rectangular shape with its longitudinal sides parallel to the central axis X (FIG. 4).

The first reflector 300c reflects the light that has entered the head unit 300. The first reflector 300c is provided over the inner surface of the head unit 300 (FIGS. 3 and 5). The first reflector 300c is made of a material that reflects light. When the light produced by the light source device 2 has a wavelength range of visible light, the material used for reflecting light is a metallic material such as silver (Ag) or aluminum (Al). When the light produced by the light source device 2 has a wavelength range of infrared light, the material used for reflecting light is a metallic material such as gold (Au).

The light that has entered the head unit 300 travels, while being repeatedly reflected from the first reflector 300c. Part of the light propagating through the head unit 300 reaches the exit hole 300b and is emitted to the outside through the exit hole 300b. The biological tissue O is then cauterized with the light that has been emitted through the exit hole 300b.

The first fixed member 32a is to be fixed relative to a first fixing member 33a of the catheter 31, which will be described later.

The first fixed member 32a is provided near the distal end portion of the head unit 300. The first fixed member 32a in an embodiment of the present disclosure has an annular shape. The first fixed member 32a is provided in the outer circumferential surface of the head unit 300 such that the first fixed member 32a has a rotational symmetry around the central axis X of the head unit 300.

In an embodiment of the present disclosure, the material of the first fixed member 32a is magnetic material. The magnetic material may be either paramagnetic or ferromagnetic, and it is selected based on the type of the material of the first fixing member 33a which will be described later. The material of the first fixed member 32a in an embodiment of the present disclosure is paramagnetic.

The second fixed member 32b is to be fixed relative to a second fixing member 33b of the catheter 31 which will be described later.

The second fixed member 32b is provided near the proximal end portion of the head unit 300. The second fixed member 32b is in the form of a rectangular cuboid.

In an embodiment of the present disclosure, the material of the second fixed member 32b is magnetic material. The magnetic material may be either paramagnetic or ferromagnetic. It is selected based on the type of the material of the second fixing member 33b which will be described later. The second fixed member 32b in an embodiment of the present disclosure is made of a ferromagnetic material with spontaneous magnetization. FIG. 2 and other figures illustrate some of the magnetic field lines from the second fixed member 32b.

Here, a relative position among the exit hole 300b, the first fixed member 32a, and the second fixed member 32b will be described. The exit hole 300b is located between the first fixed member 32a and the second fixed member 32b (FIGS. 2 and 3). The exit hole 300b and the second fixed member 32b are located to have the same azimuth relative to the central axis X.

The probe 30 according to an embodiment of the present disclosure has been described hereinabove, however, this is just an example and is not limited thereto. For example, the head unit 300 according to an embodiment of the present disclosure has a hollow cylindrical portion, however it is not limited to a cylindrical shape and may have a portion with a prism shape. Likewise, the exit hole 300b according to an embodiment of the present disclosure has a rectangular shape. However, it is not limited to this shape, and may be designed as appropriate depending on an area of the biological tissue to be cauterized. Furthermore, the number of the exit hole 300b is not limited to one, and two or more exit holes may be provided.

<Catheter>

The catheter 31 includes a main body 310, the first fixing member 33a, the second fixing member 33b, and a second reflector 311.

The main body 310 is an elongated tubular member. The main body 310 is made of a material such as a flexible resin. The main body 310 in an embodiment of the present disclosure is formed of a transparent material. One of the end portions of the main body 310 which is to be inserted into the living body is referred to as a "distal end portion of the catheter 31," and the other end portion to be grasped by a surgeon is referred to as a "proximal end portion of the catheter 31."

The first fixing member 33a is located within an opening portion in the distal end portion of the main body 310. In an embodiment of the present disclosure, the material of the first fixing member 33a is magnetic material. Although the magnetic material may be either paramagnetic or ferromagnetic, the magnetic material that attracts and is attracted by the first fixed member 32a is to be selected.

The first fixing member 33a in an embodiment of the present disclosure is made of a ferromagnetic material with spontaneous magnetization. FIG. 2 and other figures illustrate some of the magnetic field lines from the first fixing member 33a. This, causes the first fixing member 33a and the first fixed member 32a to attract each other through a magnetic force, thereby fixing the position of the first fixed member 32a.

The second fixing member 33b is provided to the catheter 31 at a distance from the first fixing member 33a. The distance between the first fixing member 33a and the second fixing member 33b is determined to be approximately equal to the distance between the first fixed member 32a and the second fixed member 32b.

The second fixing member 33b has an annular shape and is provided in the outer circumferential surface of the catheter 31. In an embodiment of the present disclosure, the material of the second fixing member 33b is magnetic. The magnetic material may be either paramagnetic or ferromagnetic, and the magnetic material that attracts and is attracted by the second fixed member 32b is selected. The material of the second fixing member 33b in an embodiment of the present disclosure is paramagnetic. This causes the second fixing member 33b and the second fixed member 32b with spontaneous magnetization to attract each other through a magnetic force, thereby fixing the position of the second fixed member 32b.

It should be noted that the "fixed members" and the "fixing members" are interchangeable. In this specification, the first fixed member 32a, the second fixed member 32b, the first fixing member 33a, and the second fixing member 33b are examples of a "first fixing member," a "second fixing member," a "third fixing member," and a "fourth fixing member," respectively.

An embodiment of the present disclosure describes an aspect in which the first fixed member 32a and the first fixing member 33a are magnetic. However, any means other than a magnetic force may be used, as long as the positions of the first fixed member 32a and the first fixing member 33a can be fixed relative to each other. The same applies to the second fixed member 32b and the second fixing member 33b.

Additionally, an embodiment of the present disclosure describes an aspect in which the first fixed member 32a is paramagnetic and the first fixing member 33a is ferromagnetic. However, the present disclosure is not limited thereto, and other configurations may be used as long as the first fixed member 32a and the first fixing member 33a attract each other through a magnetic force.

For example, the first fixed member 32a may be ferromagnetic and the first fixing member 33a may be paramagnetic. Alternatively, both of the first fixed member 32a and the first fixing member 33a may be ferromagnetic. In this case, the directions in which the first fixed member 32a and the first fixing member 33a face should be determined such that they attract each other. The same applies to the second fixed member 32b and the second fixing member 33b.

The second reflector 311 reflects the light that has been emitted through the exit hole 300b and has passed through the biological tissue O, toward the biological tissue O. The second reflector 311 is provided between the first fixing member 33a and the second fixing member 33b. The second reflector 311 should be positioned to face at least the exit hole 300b, with the positions of the first fixed member 32a and the second fixed member 32b being fixed by the first fixing member 33a and the second fixing member 33b, respectively (FIG. 2).

The second reflector 311 in an embodiment of the present disclosure is formed over the entire inner circumferential surface of the main body 310 in a range between the first fixing member 33a and the second fixing member 33b. The second reflector 311 is made of a material similar to that of the first reflector 300c. The second reflector 311 may be formed not only on the inner circumferential surface of the main body 310 but also in the hollow portion of the main body 310 by filling a material similar to that of the first reflector 300c. Alternatively, when the main body 310 is made of a material that blocks light, the second reflector 311 should then be formed over the inner circumferential surface of the main body 310.

==Alignment==

Cauterization of the biological tissue O using the cautery system 1 according to an embodiment of the present disclosure is performed with the cautery device 3 being in a state illustrated in FIG. 2. The state of the cautery device 3 illustrated in FIG. 2 is hereinafter referred to as "aligned state." The side of a surface of the biological tissue O on which the head unit 300 is placed during cauterization is referred to "front surface", and the side of a surface on which a catheter is placed is referred to as a "back surface." Referring to FIGS. 2 and 7 to 9, an exemplified procedure for achieving the aligned state will be described.

Figure 7:
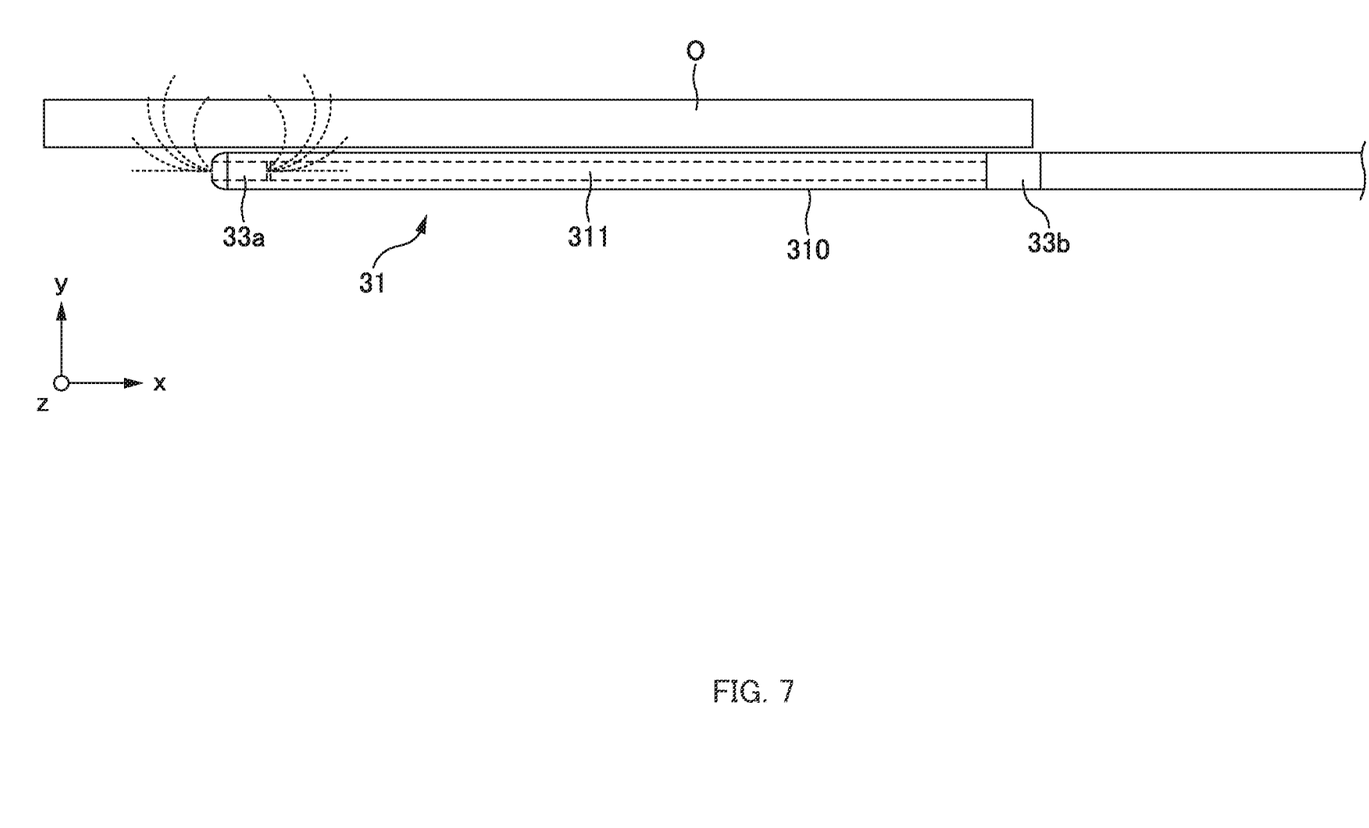
FIG. 7 is a diagram for explaining a process of positioning a cautery device according to a first embodiment.

First, the catheter 31 is, for example, inserted through a femoral artery and placed at the biological tissue O to be cauterized (e.g., inside the left ventricle) (FIG. 7). The catheter 31 is placed such that the second reflector 311 faces an area of the biological tissue O to be cauterized.

Figure 8:
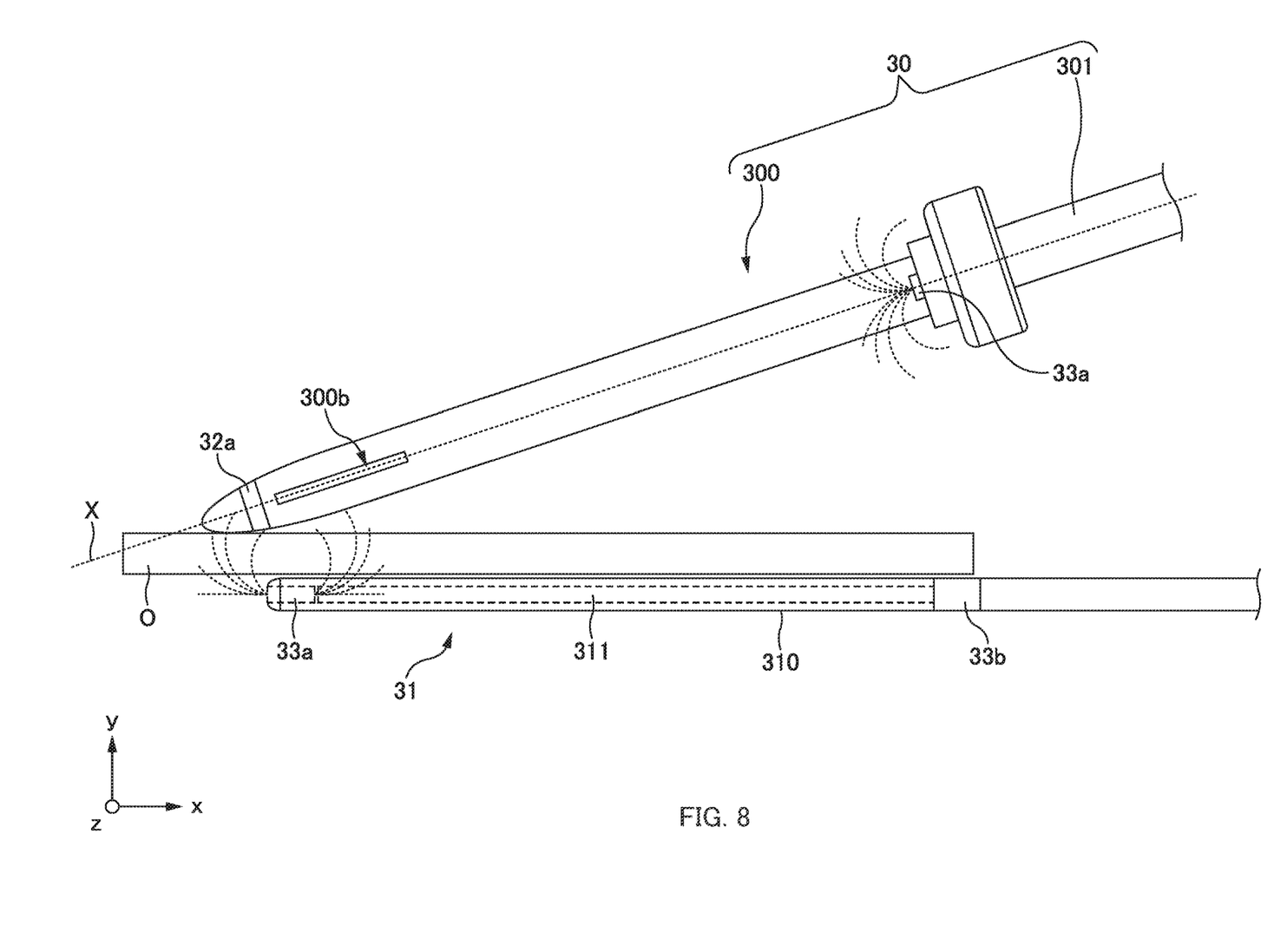
FIG. 8 is a diagram for explaining a process of positioning a cautery device according to a first embodiment.

Next, the probe 30 is inserted into the living body and placed at the biological tissue O to be cauterized (e.g., outside the left ventricle). When the first fixed member 32a of the head unit 300 of the probe 30 approaches the first fixing member 33a, the first fixed member 32a is fixed relative to the first fixing member 33a by virtue of forces of mutual attraction between the first fixed member 32a and the first fixing member 33a (FIG. 8).

It should be noted that the first fixed member 32a and the second fixing member 33b in an embodiment of the present disclosure are both paramagnetic, and thus are not magnetized. Accordingly, the first fixed member 32a has no chance of being fixed accidentally relative to the second fixing member 33b.

Figure 9:
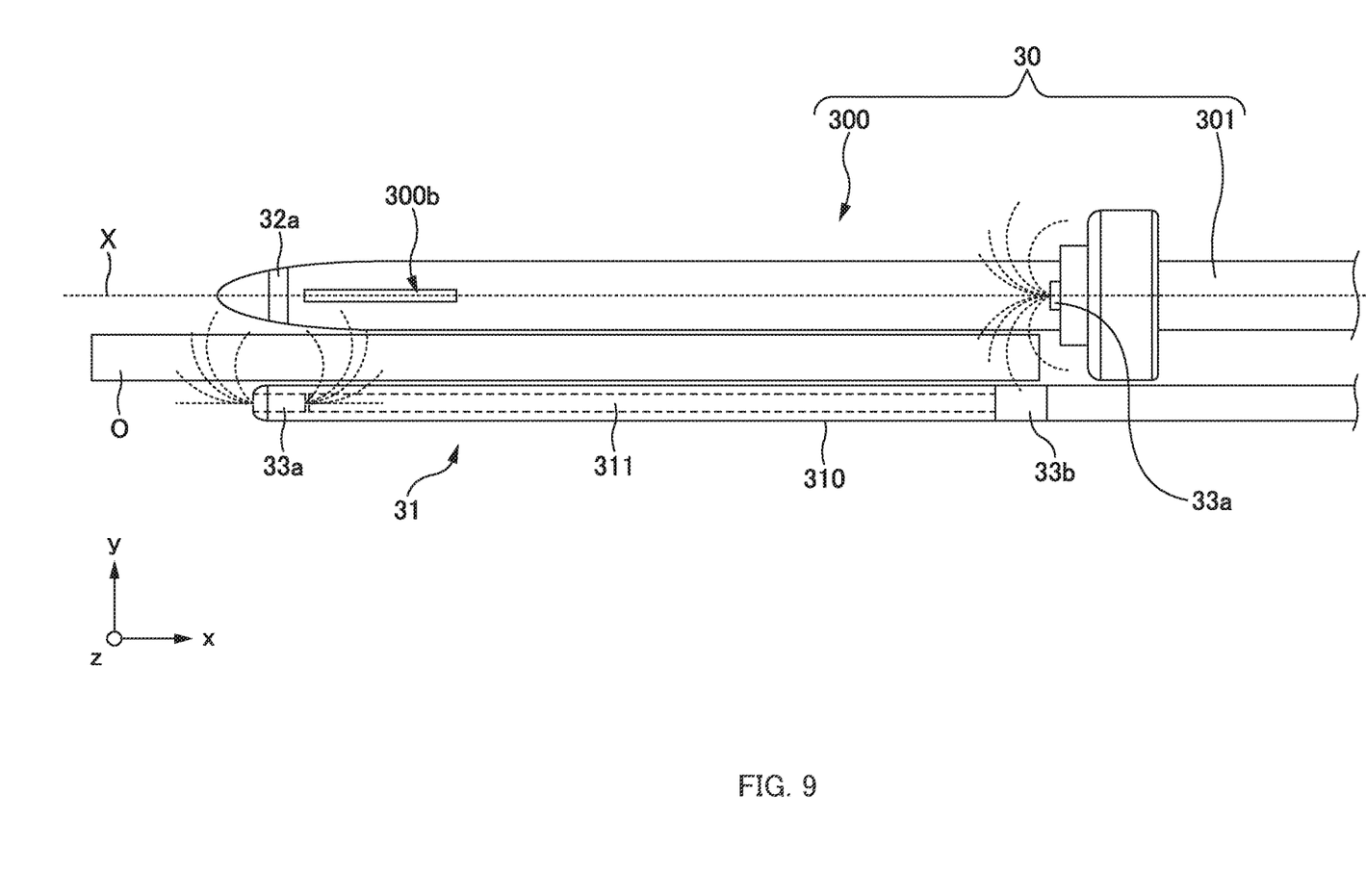
FIG. 9 is a diagram for explaining a process of positioning a cautery device according to a first embodiment.

Next, the second fixed member 32b of the head unit 300 of the probe 30 is positioned relative to the second fixing member 33b. Specifically, from the state illustrated in FIG. 8, the orientation of the head unit 300 is changed such that the central axis X of the head unit 300 becomes parallel to the front surface of the biological tissue O, without changing the position of the first fixing member 33a (FIG. 9).

Next, the head unit 300 is turned about the central axis X of the head unit 300 until the second fixed member 32b moves to a position at which the second fixed member 32b faces the second fixing member 33b. This allows the position of the second fixed member 32b to be fixed relative to the second fixing member 33b.

It should be noted that the first fixed member 32a in an embodiment of the present disclosure has an annular shape. Accordingly, even if the head unit 300 turns about the central axis X from the state in FIG. 9, the positions of the first fixed member 32a and the first fixing member 33a are fixed without being separated from each other.

The aforementioned procedure results in the alignment illustrated in FIG. 2. In the state of the cautery device 3 illustrated in FIG. 2, the first fixed member 32a is fixed relative to the first fixing member 33a and the second fixed member 32b is fixed relative to the second fixing member 33b. In other words, the head unit 300 and the catheter 31 are fixed relative to each other at two positions, while sandwiching the biological tissue O therebetween.

As described above, the exit hole 300b and the second fixed member 32b are arranged so as to have the same azimuth relative to the central axis X. Accordingly, in the aligned state, the exit hole 300b is positioned in the area of the biological tissue O to be cauterized. In other words, once the aligned state has been achieved, the exit hole 300b is automatically located in the area of the biological tissue O to be cauterized.

In this state, by emitting light through the exit hole 300b, the biological tissue O is cauterized. Furthermore, in this state, the area of the biological tissue O to be cauterized becomes uniform in thickness by being sandwiched between the probe 30 and the catheter 31. This makes it possible to achieve uniform cauterization in the area of the biological tissue O to be cauterized.

While the aforementioned example describes an aspect in which the catheter 31 is placed at a given position relative to the biological tissue O and then the head unit 300 is aligned, the present disclosure is not limited thereto. In contrast, the head unit 300 may be placed at a given position relative to the biological tissue O and then the catheter 31 may be aligned.

Second Embodiment

Figure 10:
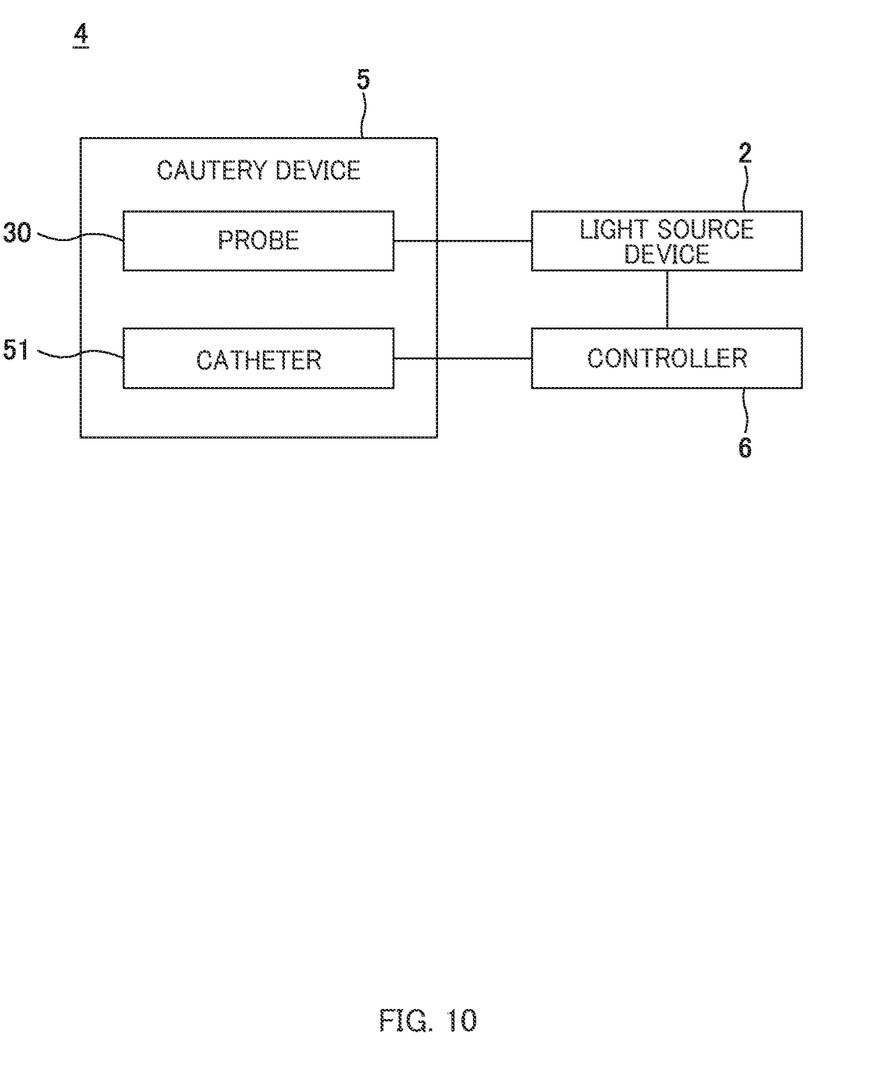
FIG. 10 is a block diagram for explaining a configuration of a cautery system according to a second embodiment.

FIG. 10 is a block diagram for explaining a configuration of a cautery system 4 according to an embodiment of the present disclosure. The cautery system 4 of an embodiment of the present disclosure further includes a controller 6, as compared with the first embodiment. Furthermore, a cautery device 5 of an embodiment of the present disclosure includes a catheter 51 with a different structure.

<Catheter>

Figure 11:
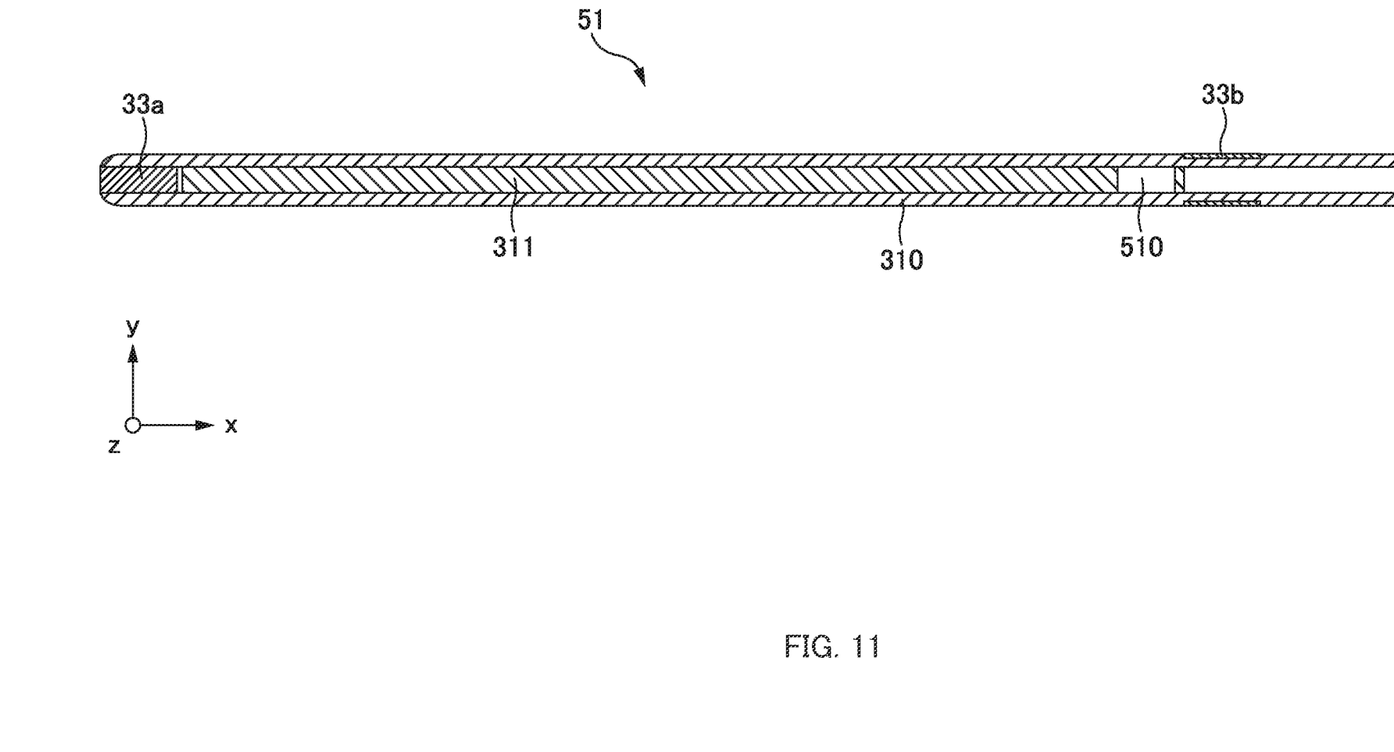
FIG. 11 is a cross-sectional view for explaining a structure of a catheter according to a second embodiment.

FIG. 11 is a cross-sectional view for explaining a structure of the catheter 51 of an embodiment of the present disclosure. The catheter 51 of an embodiment of the present disclosure further includes an optical sensor 510. The optical sensor 510 detects the light that has been emitted through the exit hole 300b. The optical sensor 510 sends a signal corresponding to an illuminance of the detected light to the controller 6.

The optical sensor 510 is provided between the second reflector 311 and the second fixing member 33b in the hollow main body 310. The arrangement of the optical sensor 510 is not limited thereto, and the optical sensor 510 may be disposed at any location as long as it can detect the light emitted through the exit hole 300b.

[Controller]

The controller 6 controls an intensity of the light produced by the light source device 2, according to an output result in terms of the intensity of the light detected by the optical sensor 510. When the output result given by the optical sensor 510 is lower than a predetermined illuminance, then the controller 6 controls the light source device 2 to increase the intensity of the light to be produced by the light source device 2. On the other hand, when the output result given by the optical sensor 510 is higher than the predetermined illuminance, then the controller 6 controls the light source device 2 to decrease the intensity of the light to be produced by the light source device 2. This enables more uniform cauterization of the area of the biological tissue O to be cauterized.

Third Embodiment

A cautery system according to an embodiment of the present disclosure is different from the one according to the second embodiment in the processing performed by the controller.

The controller of an embodiment of the present disclosure controls a spectrum characteristic of light produced by the light source device 2, according to an output result in terms of a spectrum characteristic of the light detected by the optical sensor 510. Specifically, when the spectrum characteristic of the light detected by the optical sensor 510 is different from a predetermined spectrum characteristic, the controller controls the light source device 2 such that the spectrum characteristic achieves the predetermined spectrum characteristic.

For example, when an illuminance of the light, of a certain wavelength band, detected by the optical sensor 510 is insufficient relative to the predetermined illuminance, the controller controls the light source device 2 so as to increase the intensity of the light of the that wavelength band in which the illuminance is insufficient. On the other hand, when an illuminance of the light, of a certain wavelength band, detected by the optical sensor 510 is excessive relative to the predetermined illuminance, the controller controls the light source device 2 so as to decrease the intensity of the light of that wavelength band in which the illuminance of light is excessive.

By controlling the light source device 2 as such, it is possible to apply light having an optimum spectrum characteristic to biological tissue. The use of the light with an optimum spectrum characteristic stabilizes the cauterizing temperature with respect to tissue, and enables uniform cauterization without scorching the surface of the tissue.

Embodiments of the present disclosure described above are simply to facilitate understanding of the present disclosure and are not in any way to be construed as limiting the present disclosure. The present disclosure may variously be changed or altered without departing from its essential features and encompass equivalents thereof.

SUMMARY

In the cautery system 1 according to the first embodiment, the cautery device 3 is for the biological tissue O, comprising the probe 30 having the head unit 300 to be inserted into a living body, the head unit configured to emit light to cauterize the biological tissue O, the head unit 300 having the first fixed member 32a, the second fixed member 32b, and the exit hole 300b located between the first fixed member 32a and the second fixed member 32b, the exit hole 300b allowing the light to be emitted therethrough; and the elongated catheter 31 configured to sandwich the biological tissue O between the probe 30 and the catheter 31 to thereby support the biological tissue O, the catheter 31 having the first fixing member 33a configured to fix the first fixed member 32a and the second fixing member 33b configured to fix the second fixed member 32b. The same applies to the second embodiment.

Such configuration makes it possible to sandwich the biological tissue to be cauterized between the probe 30 and the catheter 31. Accordingly, even when the thickness of an area of the biological tissue O to be cauterized varies in part, the biological tissue O to be cauterized can have a thickness that is substantially uniform as well as reduced by being sandwiched to be compressed, thereby being able to allow the light from the probe to be more likely to pass therethrough. Then, in this state, the cautery device 3 applies light to the biological tissue O, thereby being able to cauterize an area of the biological tissue O to be cauterized, in a uniform manner while passing through the tissue.

The first fixed member 32a and the first fixing member 33a attract each other through a magnetic force, and the second fixed member 32b and the second fixing member 33b attract each other through a magnetic force. This enables reliable alignment by virtue of the pull force of the magnets even when the catheter that has been inserted into a living body cannot be located.

The catheter 31 further includes the second reflector 311 disposed between the first fixing member 33a and the second fixing member 33b, the second reflector 311 being configured to reflect light emitted through the exit hole 300b toward the biological tissue O. Such configuration makes it possible to irradiate both sides of the biological tissue O with the light for cauterization. Accordingly, even when the thickness of an area of the biological tissue to be cauterized varies in part, the light from the reflector 311 returns to the biological tissue, to thereby increase the amount of light applied inside the biological tissue even in a thicker part. This improves the irradiation efficiency and enables more uniform cauterization in the thickness direction of the biological tissue O.

In the cautery system 4 according to the second embodiment, the catheter 51 further includes the optical sensor 510 configured to detect light emitted through the exit hole 300b. Such configuration makes it possible to adjust the intensity of light emitted through the exit hole 300b such that the illuminance of light near the catheter 51 has a predetermined value, according to the illuminance of light outputted from the optical sensor 510. This makes it possible to uniformly cauterize an area of the biological tissue O to be cauterized, without scorching the tissue surface, by stabilizing the cauterizing temperature for tissue with an optimum amount of irradiation light.

The cautery system 4 according to the second embodiment comprises the aforementioned cautery device 5, the light source device 2 configured to produce light to be emitted through the exit hole 300b, and the controller 6 configured to control an intensity of light produced by the light source device 2, according to an output result in terms of an illuminance of light detected by the optical sensor 510. Such configuration makes it possible to automatically adjust the intensity of light emitted through the exit hole 300b such that the illuminance of light near the catheter 51 has a predetermined value, based on the illuminance of light outputted from the optical sensor 510. This makes it possible to uniformly cauterize an area of the biological tissue O to be cauterized, without scorching the tissue surface, by stabilizing the cauterizing temperature for tissue with an optimum amount of irradiation light. Furthermore, this improve the convenience of the cautery system 4.

The cautery system according to the third embodiment comprises the aforementioned cautery device 5, the light source device 2 configured to produce light to be emitted through the exit hole 300b, and a controller configured to control a spectrum characteristic of the light produced by the light source device 2, according to an output result in terms of a spectrum characteristic of light detected by the optical sensor 510. Such configuration makes it possible to automatically adjust the spectral characteristic of light emitted through the exit hole 300b such that the amount of light corresponding to the wavelength band has a predetermined value in the vicinity of the catheter 51, according to the spectral characteristic of the light outputted from the optical sensor 510. Accordingly, the biological tissue can be irradiated with light having an optimum spectral characteristic. The use of the light with an optimum spectral characteristic enables uniform cauterization by stabilizing the cauterizing temperature for tissue, without scorching the tissue surface.

The present disclosure is directed to provision of cautery devices capable of uniformly cauterizing a given area of biological tissue.

The present disclosure makes it possible to uniformly cauterize a given area of biological tissue.

What is claimed is:

1. A cautery device for biological tissue, comprising:
   a probe including a head unit, the head unit being configured to be inserted into a living body to emit light for cauterizing the biological tissue, the head unit including a first fixing member, a second fixing member, an exit hole, and a first reflector, the exit hole being located between the first fixing member and the second fixing member, the exit hole allowing the light to be emitted therethrough; and
   an elongated catheter configured to sandwich the biological tissue between the probe and the catheter, to thereby support the biological tissue, the catheter including a third fixing member configured to fix the first fixing member and a fourth fixing member configured to fix the second fixing member,
   wherein the head unit has a hollow body and the first reflector is arranged along an inner surface of the hollow body and operates to reflect light that enters the head unit.

2. The cautery device according to claim 1, wherein the first fixing member and the third fixing member attract each other through a magnetic force, and the second fixing member and the fourth fixing member attract each other through a magnetic force.

3. The cautery device according to claim 1, wherein the catheter further includes a reflector disposed between the third fixing member and the fourth fixing member, the reflector being configured to reflect light emitted through the exit hole, toward the biological tissue.

4. The cautery device according to claim 1, wherein the catheter further includes an optical sensor configured to detect light emitted through the exit hole.

5. A cautery system for biological tissue, comprising:
   the cautery device according to claim 4;
   a light source device configured to produce light to be emitted through the exit hole; and
   a controller configured to control an intensity of light produced by the light source device according to an illuminance of the light detected by the optical sensor.

6. A cautery system for biological tissue, comprising:
   the cautery device according to claim 4;
   a light source device configured to produce light to be emitted through the exit hole; and
   a controller configured to control a spectrum characteristic of the light produced by the light source device according to a spectrum characteristic of the light detected by the optical sensor.

* * * * *